United States Patent
Hill et al.

(10) Patent No.: US 7,398,126 B2
(45) Date of Patent: Jul. 8, 2008

(54) DRUG DISPENSING MEDICAL ELECTRODE LEAD AND METHOD FOR MAKING SAME

(75) Inventors: Rolf Hill, Jarfalla (SE); Sven Kalling, Täby (SE); Martin Obel, Danderyd (SE); Maria Wargelius, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 643 days.

(21) Appl. No.: 10/473,552

(22) PCT Filed: Mar. 25, 2002

(86) PCT No.: PCT/SE02/00601

§ 371 (c)(1),
(2), (4) Date: Apr. 19, 2004

(87) PCT Pub. No.: WO02/078782

PCT Pub. Date: Oct. 10, 2002

(65) Prior Publication Data

US 2004/0172117 A1    Sep. 2, 2004

(30) Foreign Application Priority Data

Mar. 29, 2001    (SE) .................... 0101154

(51) Int. Cl.
*A61N 1/05*    (2006.01)
*A61K 9/22*    (2006.01)

(52) U.S. Cl. .............. 607/120; 604/890.1; 604/891.1

(58) Field of Classification Search .......... 604/890.1, 604/891.1; 607/120

See application file for complete search history.

(56) References Cited

U.S. PATENT DOCUMENTS

| | | | |
|---|---|---|---|
| 4,506,680 | A | 3/1985 | Stokes |
| 4,577,642 | A | 3/1986 | Stokes |
| 4,711,251 | A | 12/1987 | Stokes |
| 4,816,262 | A | 3/1989 | McMullen |
| 4,819,661 | A | 4/1989 | Heil et al. |
| 4,819,662 | A | 4/1989 | Heil et al. |
| 4,922,926 | A | 5/1990 | Hirschberg et al. |
| 4,972,848 | A | 11/1990 | Domenico et al. |
| 5,002,067 | A | 3/1991 | Berthelsen et al. |
| 5,003,992 | A | 4/1991 | Holleman et al. |
| 5,103,837 | A | 4/1992 | Weidlich et al. |
| 6,038,482 | A | 3/2000 | Vachon |
| 6,207,181 | B1 * | 3/2001 | Herrmann ............. 424/448 |

FOREIGN PATENT DOCUMENTS

| | | |
|---|---|---|
| EP | 0334 306 | 3/1989 |
| WO | WO98/15317 | 4/1998 |

* cited by examiner

*Primary Examiner*—Carl H. Layno
*Assistant Examiner*—Yun Haeng Lee
(74) *Attorney, Agent, or Firm*—Schiff Hardin LLP

(57) ABSTRACT

In an electrically conductive lead adapted for implantation in a human or animal body, and a method for making such a lead, a drug-dispensing member is disposed at a distal end portion of the lead, at which an electrode member is disposed that is adapted to emit and/or sense electrical signals associated with medical therapy. The drug-dispensing member has a configuration so that, after implantation, the amount of drug released into the body per time unit is automatically controlled to smoothly vary with time from al larger amount to a smaller amount in accordance with a predetermined relationship of the amount of drug released as a function of time.

34 Claims, 3 Drawing Sheets

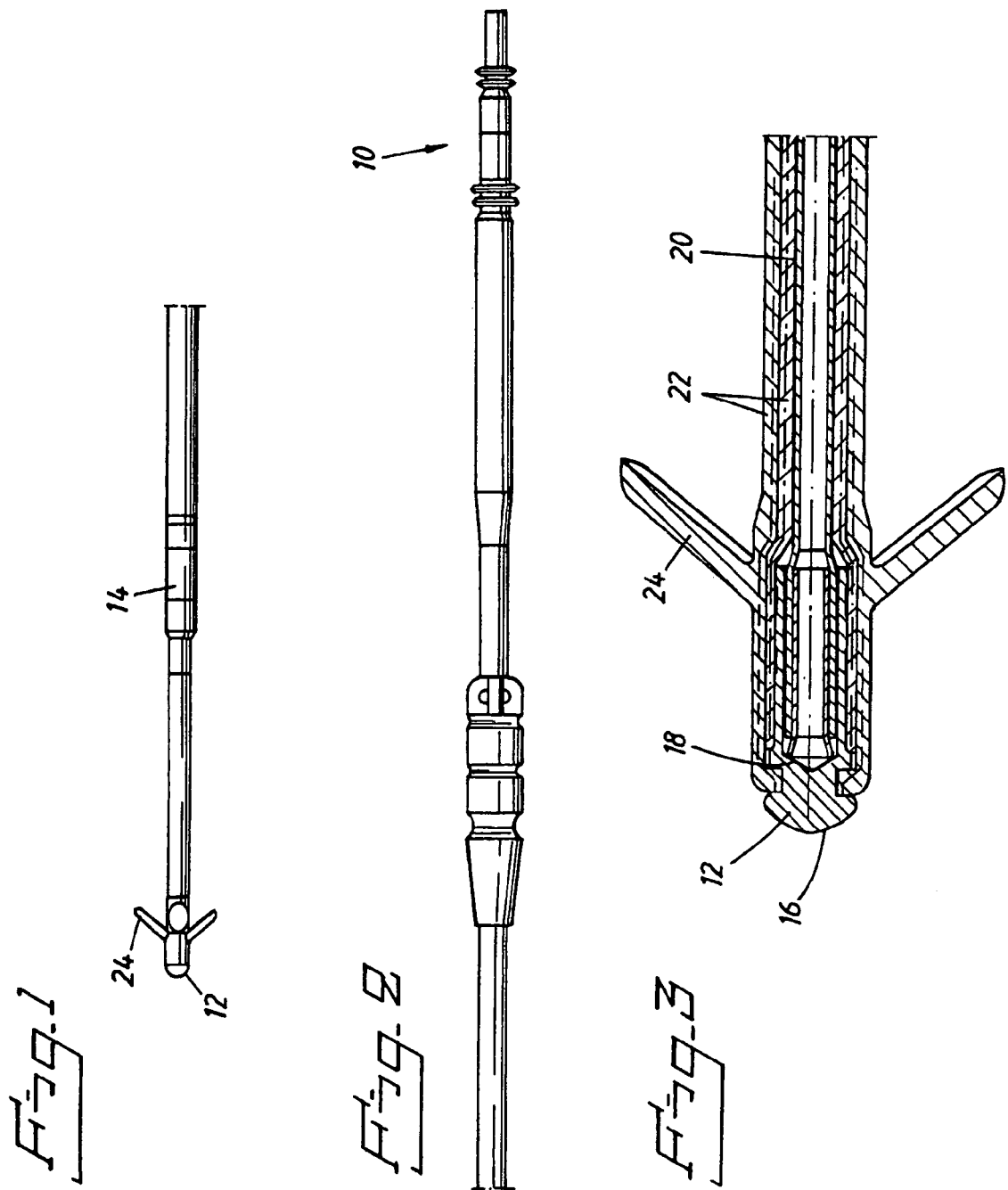

DRUG DISPENSING MEDICAL ELECTRODE LEAD AND METHOD FOR MAKING SAME

BACKGROUND OF THE INVENTION

1. Field of the Invention

The present invention relates to leads which are electrically conductive and which are suitable to be implanted in a human or animal body. Such leads may for example be used to conduct electrical stimulation pulses from an implanted heart stimulating device to the heart of said human or animal body. Leads may, however, also be used in connection with other kinds of medical devices. Preferably the heart electrode leads are adapted to be insertable via the vascular system into the human or animal heart. Such heart electrode leads are particularly suitable for intracardial stimulation of the heart with the help of an implantable pacemaker or defibrillator. The invention concerns both a lead as such and a method of producing a lead.

2. Description of the Prior Art

A large number of different leads are known in the art. A lead normally has a proximal end portion to be connected to a device, for example a heart-stimulating device, and a distal end portion that is to be positioned at a predetermined position in the body, usually in or at the heart. A heart electrode lead may be unipolar or bipolar. A unipolar lead has only one single electrode member usually arranged at the tip of the distal end portion of the lead. A bipolar lead has two electric poles. Also this kind of electrode lead usually has one electrode member located at the tip at the distal end portion of the lead. The lead has at least one electric conductor, which extends from the proximal end portion to the electrode member at the distal end portion.

For example in the case of a lead for a heart stimulating device, it is known that when a lead has been implanted into or at the heart, the stimulation threshold is higher during a certain time after the implantation and then becomes lower. It is also known that this stimulation threshold may be lowered by providing a drug, such as a steroid, at the distal end portion of the lead. The drug is arranged such that it will be dispensed to the surrounding body tissue over a period of time.

U.S. Pat. No. 5,103,837 describes the use of a coating including a drug [is provided] on an electrode member of titanium nitride.

U.S. Pat. No. 4,819,661 describes different leads with helical fixation members. A drug impregnated matrix, preferably of a biocompatible silicon adhesive, is positioned in a cavity at the distal end portion of the lead.

U.S. Pat. No. 5,003,992 also describes a lead with a helical fixation member. A plug made of a polymer with a drug is located in a cavity at the distal end portion of the lead.

U.S. Pat. No. 5,002,007 discloses a lead with a helical fixation member. A cylindrical plug fabricated of a silicon-based polymer incorporating an anti-inflammatory drug is positioned in a cavity at the distal end portion of the lead. The fixation helix may also be provided with a groove along which the drug may be released.

U.S. Pat. No. 4,972,848 describes a lead with a helical fixation means. A release device made of a polymer and incorporating a drug is provided in a cavity at the distal end portion of the lead, U.S. Pat. No. 4,506,680 describes a sintered metal electrode member located at the distal end of the lead. In a cavity inside of this electrode member a polymer impregnated with a drug is positioned.

U.S. Pat. No. 4,577,642 describes a lead with a porous sintered metal electrode member located at the distal end portion of the lead. In a cavity inside of the electrode member, a drug is retained in a solid plug or a powder wherein the drug is compounded with an appropriate molecular sieve material.

U.S. Pat. No. 6,038,482 discloses a lead with an electrode member positioned at the distal end portion of the lead. The electrode member has an interior cavity and a bore extending between the interior cavity and the exterior surface of the electrode member. A matrix member with a drug is positioned in the interior cavity. The exterior surface of the electrode member is coated with a wetting agent with the same drug as in the matrix. Also the bore is filled with a wetting agent with the same drug as in the matrix. According to this document, a tiered delivery of the drug is achieved, where the drug on the exterior surface and in the bore elutes within approximately a 24 hour period and the drug in the matrix elutes for a much longer term measured in months or years.

U.S. Pat. No. 4,819,612 describes a cardiac pacing lead that includes a porous element tip electrode that can be loaded with a drug that will be eluted upon implantation. One or several matrices can be housed in a recess behind the tip electrode for continuous drug elution.

European Application 334 306 describes a transdermal adhesive for diminishing release of active substances.

SUMMARY OF THE INVENTION

An object of the present invention is to provide a lead that includes a drug and that is arranged such that an efficient utilization of the drug is achieved. A second object is to provide a method of producing such a lead.

The first object is achieved in accordance with the invention in an electrically conductive lead suitable for implantation in a human or animal body, the lead having a proximal end adapted for attachment to a device for generating medical therapy, a distal end portion at which at least one electrode member is disposed for emitting and/or sensing electrical signals, an elongated body extending between the proximal end portion and the distal end portion, and a drug-dispensing member positioned at the distal end portion and including a drug-for release into the human or animal body, the drug-dispensing member being configured so that a surface thereof is exposed at an exterior of the lead and so that, after implantation, the amount of drug that is released into the body per time unit is automatically controlled to smoothly vary with time from a larger amount to a smaller amount in accordance with a predetermined relationship of the amount of drug released as a function of time.

Because the drug-dispensing member is designed in this manner, the drug released into the body can be controlled in an optimal way. It is thus, for example, possible to control that a certain high amount of drug is released immediately after implantation of the lead, whereafter the amount of drug released per time unit smoothly decreases in a controlled manner to a smaller amount.

In a preferred embodiment of the lead according to the invention, the drug is or contains an anti-inflammatory agent. Such a drug may be used, for example, to decrease the stimulation threshold for a pacemaker lead.

In a further embodiment, the design of the drug-dispensing member is such that the decrease in the amount of drug released into the body from a maximum amount released during the first hours after implantation to an amount which is about ⅓ of this maximum amount takes at least 24 hours. Such a decrease in the amount of drug released is advantageous in many cases where a lead is implanted into a body.

In another embodiment, the distal end portion has at least one cavity having an opening arranged at an exterior surface of the distal end portion of the lead such that the cavity is open to the exterior of the distal end portion, wherein said drug-dispensing member is located in said cavity, and wherein the shape of the cavity is such that the amount of drug released into the body per time unit is controlled by said shape. Such a lead may be made in a relatively simple manner. Because the drug-dispensing member is located in the cavity, it is arranged well protected against accidental damage.

In a further embodiment, the shape of the cavity is such that the cross-sectional area of the cavity varies smoothly from a maximum area at said opening at the exterior surface of the distal end portion to an essentially smaller area at a position further into said cavity. Such a lead is relatively easy to make and the release of the drug may thus be controlled in a simple manner. By cross-sectional area is meant the area of the cross-section perpendicular to the main direction in which the elongated lead extends.

In a further embodiment, the shape of the cavity is such that the maximum cross-sectional area at said opening at the exterior surface of the distal end portion is at least twice the smallest cross-sectional area of said cavity. With such a design, the amount of drug released can be controlled to decrease to a predetermined amount.

In another embodiment, the at least one electrode member has a first surface portion facing the exterior of the distal end portion of the lead and a second surface portion facing the interior of the lead, wherein the cavity is located such that the opening is located in said first surface portion. The drug may thus be released at the very end tip of the lead.

In a further embodiment, the cavity is located such that the cavity does not extend to the second surface portion, such that it does not extend all the way through the electrode member, and the cavity does not have any opening toward the interior of the lead. Such an electrode member is relatively easy to produce. Furthermore, there is no risk that body fluids enter into the interior of the lead via the cavity.

In still another embodiment, the cavity extends from the first surface portion and has a minimum cross-sectional area at an intermediate position of said cavity which is smaller than the cross-sectional area of the cavity at a position located proximal of said intermediate position. A larger space may in this manner be formed inside of a narrower part of the cavity. The larger space may, for example, be used to hold a drug intended for a long-term release.

In a further embodiment, the cavity is positioned such that the opening is located at the distal end tip of the lead and such that the cavity extends in the longitudinal direction of the lead. In such a lead, the cavity may be symmetrically arranged in the distal portion of the lead.

In another embodiment, the distal end portion has a number of such cavities, which together are designed such that the amount of drug released is controlled to vary according to a predetermined relationship.

In a further embodiment, the drug-dispensing member or members are formed in a material that is soluble or resorbable in body fluids. Such a material is particularly suitable for holding the drug.

In another embodiment, the electrode member forms the distal end portion of the lead and said drug-dispensing member is positioned on the surface of said electrode member. In such a lead, it is not necessary to form a cavity in the electrode member.

In a further embodiment, the drug-dispensing member is formed in a material that is soluble or resorbable in body fluids and the drug-dispensing member has a shape that is such that the exterior surface area of the drug-dispensing member will decrease with time, when the drug-dispensing member is dissolved or resorbed, in such a manner that said controlled release of the drug is achieved. Instead of a particular shape of a cavity, it is thus possible to control the release of the drug by a particular design of the drug-dispensing member positioned on the surface of the electrode member.

In a further embodiment, the drug-dispensing member has a cone-like shape with a base surface attached to said electrode member and a narrow end, pointing away from the electrode member. A lead with such a drug-dispensing member may be formed in a relatively simple manner.

In a still further embodiment, the drug-dispensing member has different concentrations of the drug in different parts of the drug-dispensing member such that the amount of drug released over time is controlled at least in part by the varying concentration of the drug in the member.

In a further embodiment, different parts of the drug-dispensing member contain materials of different compositions, which are soluble or resorbable in body fluids a different rates, and the different parts are positioned such that the amount of drug released over time is controlled at least in part by the different compositions and the position of the different parts in the drug-dispensing member. The release of the drug may thus also be controlled by the actual material composition in different parts of the drug-dispensing member.

The above-noted second object is achieved in accordance with the invention in a method for producing an electrically conductive lead suitable for implantation in a human or animal body, including the steps of providing an electrically conductive lead having a proximal end portion adapted for attachment to a device for generating medical therapy, a distal end portion at which at least one electrode member is disposed for emitting and/or sensing electrical signals, and an elongated body extending between the proximal end portion and the distal end portion, and providing a drug-dispensing member at the distal end portion that includes a drug for release into the human or animal body, and configuring the drug-dispensing member so that at least a portion of the surface of the drug-dispensing member is exposed at the exterior of the lead and so that, after implantation, the amount of drug released into the body per time unit is automatically controlled to smoothly vary with time from a larger amount to a smaller amount in accordance with a predetermined relationship of the amount of drug released as a function of time.

By this method, a lead having the above-described advantages is produced. It should be noted that the method steps does not necessarily have to be performed in the order listed above. It is, of course, possible to arrange the drug-dispensing member at the distal end portion before the different parts of the lead are assembled.

DESCRIPTION OF THE DRAWINGS

FIG. 1 is a schematic side view of a distal portion of a lead according to the prior art.

FIG. 2 is a schematic side view of a proximal portion of a lead according to the prior art.

FIG. 3 is a sectional view of a distal end portion of a lead according to the prior art.

DESCRIPTION OF THE PREFERRED EMBODIMENTS

Figure 4:
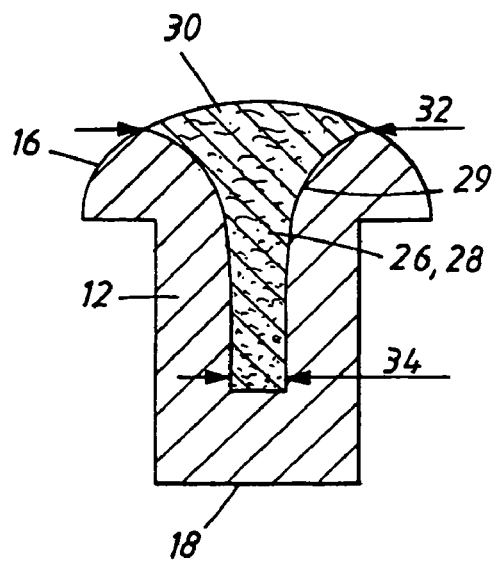
FIG. 4 is a schematic sectional view of an electrode member of a distal end portion of a lead according to an embodiment the present invention.

FIGS. 1-3 show different views of a lead according to the prior art. However, the general configuration of the lead according to the present invention can be the same as that of the prior art.

The lead has a proximal end portion (FIG. 2) with a connector 10 designed to be attached to a device, for example to a heart stimulating device. Furthermore, the lead has a distal end portion (FIG. 1) having an electrode member 12 for emitting and/or sensing electrical signals. The shown lead is bipolar and thus has a further electrode member 14. The lead has an elongated body extending between said proximal end portion and said distal end portion, i.e. the elongated body connects the two parts of the lead shown in FIG. 1 and FIG. 2.

FIG. 3 shows a sectional view of the distal end portion of the lead according to the prior art. FIG. 3 shows that the electrode member 12 has a first surface portion 16 facing the exterior of the distal end portion and a second surface portion 18 facing the interior of the lead. The electrode member 12 may for example be made of a platinum-iridium alloy. The surface may be coated with titanium nitride. The lead has at least one electric conductor 20 extending between the electrode member 12 and the connector 10. The lead also has at least one insulating member 22, for example made of silicon rubber, which encloses the electric conductor 20. The distal end portion of the lead may be provided with tines 24 to facilitate the anchoring of the electrode tip at the body tissue.

Figure 6:
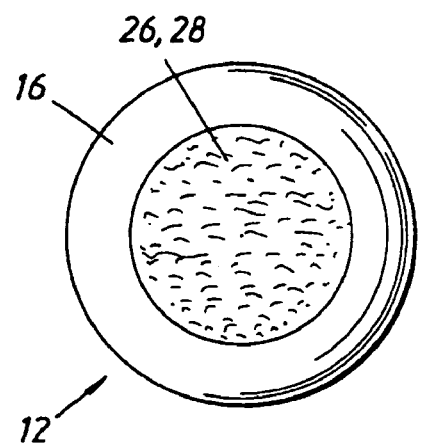
FIG. 6 shows an end view of the electrode member shown in FIGS. 4 and 5.

The first embodiment of the present invention will now be described with reference to FIGS. 4 and 6. As stated above, the general configuration of the lead may be the same as that of the prior art described above. It should be noted that the same reference numerals are used for the corresponding parts in the different figures.

The lead of the present invention is preferably of a dimension such that it is adapted to be insertable via the vascular system into a human or animal heart.

FIG. 4 thus shows an electrode member 12. The electrode member 12 has a first surface portion 16 which faces the exterior of the distal end portion of the lead. The electrode member 12 also has a second surface portion 18 facing the interior of the lead. The electrode member 12 has a cavity 28. The cavity 28 has an opening 30 arranged at an exterior surface of the distal end portion of the lead. The opening 30 is located at the distal end tip of the lead and the cavity 28 extends in the longitudinal direction of the lead. According to the shown embodiment the cavity 28 does not extend to the second surface portion 18. The cavity 28 does therefore not have any opening toward the interior of the lead. It should however be noted that according to an alternative embodiment, the cavity 28 could extend all the way through the electrode member 12.

A drug-dispensing member 26 is arranged in the cavity 28. The drug-dispensing member 26 is designed such that, when the lead has been implanted into a human or animal body, the amount of drug released into the body per time unit is automatically controlled to smoothly vary with time from a larger amount to a smaller amount in accordance with a predetermined relationship of the amount of drug released as a function of time. According to a preferred embodiment, the amount of drug released is controlled by the shape of the drug-dispensing member 26, i.e. by the shape of the cavity 28.

The drug may for example be an anti-inflammatory agent, such as a steroid, for example dexamethasone sodium phosphate. Preferably, the drug is included in a material that is soluble or resorbable in body fluids. As examples of such materials the following may be mentioned: PLA (polylactic acid), PGA (polyglycollic acid) and PDS (polydioxanone). According to one embodiment, the material may be in the form of a gel.

According to one advantageous embodiment, the drug-dispensing member 26 is designed such that the decrease in the amount of drug released into the body from a maximum amount released during the first hours after implantation to an amount which is about ⅓ of this maximum amount takes at least 24 hours.

The amount of drug released may be controlled by the shape of the drug-dispensing member 26, i.e. by the shape of the cavity 28. The curvature 29 of the side faces of the cavity 28 may thus be selected in order to achieve a predetermined amount of drug release. The cross-sectional area of the cavity 28 may vary from a maximum area 32 at the opening 30 to an essentially smaller, minimum cross-sectional area 34 at a position further into said cavity 28. Preferably, the maximum cross-sectional area 32 is at least twice the smallest cross-sectional area 34.

In addition to, or instead of, controlling the release of the drug by the shape of the cavity 28, it is possible to control the amount or drug released by the concentration of the drug in different parts of the drug-dispensing member 26. Thus a higher concentration of the drug may be arranged in the part of the drug-dispensing member 26 located closest to the opening 30.

It is also possible to control the amount of drug released by forming the drug-dispensing member 26 of different materials of different compositions in different parts of the drug-dispensing member 26. For example, materials that are more quickly resolved in body fluids may be located closer to the opening 30.

Figure 5:
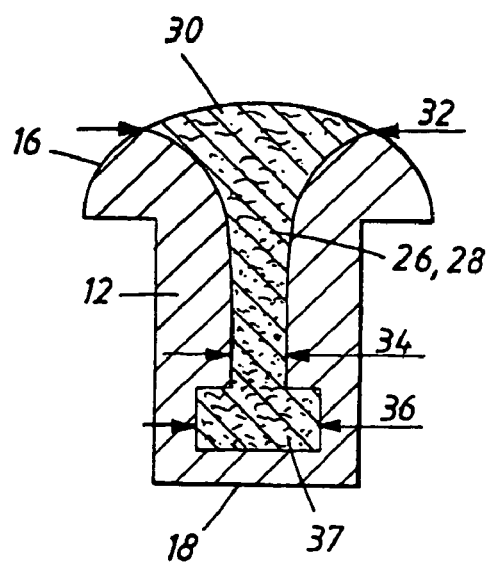
FIG. 5 shows the same view as FIG. 4 of an alternative embodiment.

FIG. 5 shows an alternative embodiment to the electrode member 12 shown in FIG. 4. FIG. 5 shows that the cavity 28 extends from the first surface portion 16 and has a minimum cross-sectional area 34 at an intermediate position of the cavity 28. This minimum cross-sectional area 34 is smaller than the cross-sectional area 36 of the cavity 28 at a position located proximal of the intermediate position. In this way an interior somewhat larger space 37 is formed. In this space 37 a larger amount of drug may be included. Since this space 37 is located inside of the major part of the cavity 28, the drug in this space 37 is suitable for long-term release.

Figure 7:
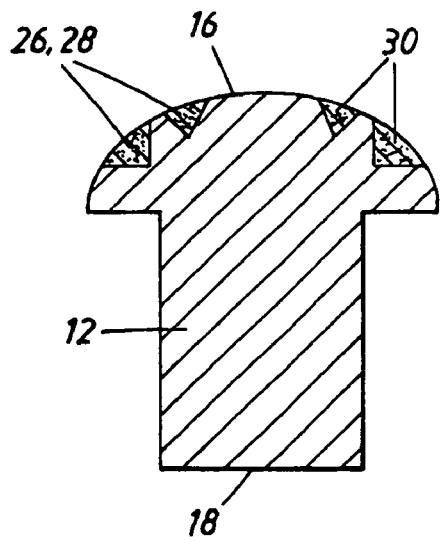
FIG. 7 shows the same view as FIG. 4 of another embodiment of the invention.
Figure 8:
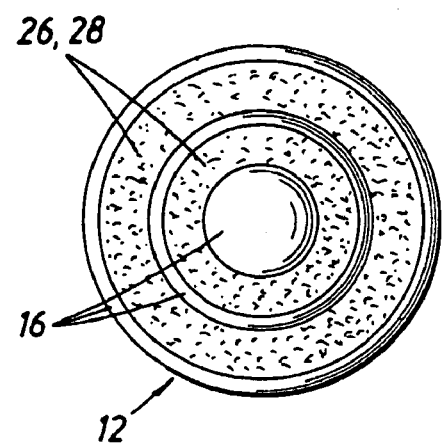
FIG. 8 shows an end view of the electrode member shown in FIG. 7.

FIGS. 7 and 8 show an electrode member 12 having a number of cavities 28. In this case the electrode member 12 comprises two such cavities 28 extending around the tip of the electrode member 12. In these cavities 28 drug-dispensing members 26 are positioned. Also the shape of these cavities 28 are designed such that an automatically controlled release of the drug is obtained.

Figure 9:
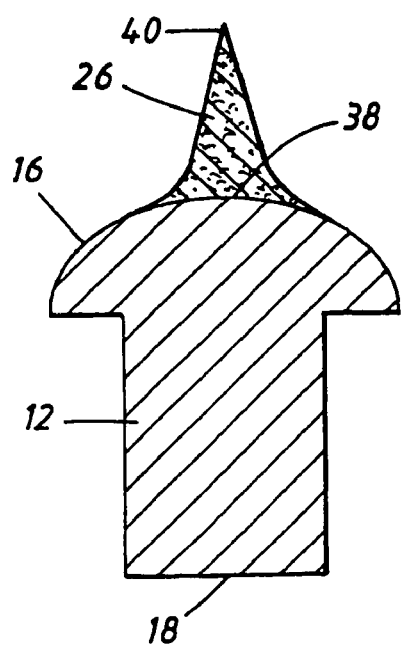
FIG. 9 shows the same view as FIG. 4 of a further embodiment of the invention.
Figure 10:
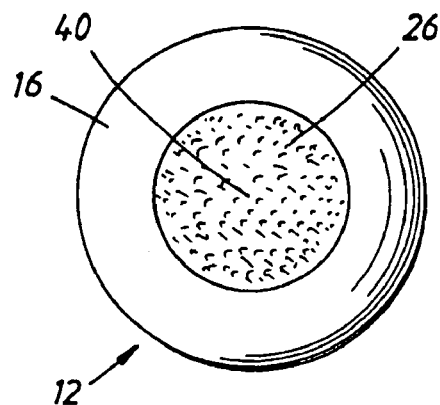
FIG. 10 shows an end view of the electrode member shown in FIG. 9.

In the embodiment shown in FIG. 9 and FIG. 10, the electrode member 12 does not have any cavity. Instead a drug-dispensing member 26 is positioned on the surface of the electrode member 12. Also in this case, the drug-dispensing member 26 is formed in a material that is soluble or resorbable in body fluids. The shape of the drug-dispensing member 26 is such that the exterior surface area of the drug-dispensing member 26 will decrease with time, when the drug-dispensing member 26 is desolved or resorbed. In the shown embodiment the drug-dispensing member 26 has a cone-like shape with a base surface 38 attached to the surface of the electrode member 12 and a narrow end 40 pointing away from the electrode member 12.

In a method according to the invention the lead is formed by providing the parts necessary for forming an electrically conductive lead having a proximal end portion designed to be attached to a device, a distal end portion, comprising at least one electrode member 12, and an elongated body extending between the proximal end portion and the distal end portion. A drug-dispensing member 26 is provided at the distal end portion. The drug-dispensing member 26 contains a drug. The drug-dispensing member 26 is designed such that the drug released into the body per time unit is automatically controlled to smoothly vary with time in accordance with a predetermined relationship such as has been described above.

The drug-dispensing member may be designed by first determining a desired relationship between the amount of drug released and time after implantation, and then designing the drug-dispensing member such that the relationship will be fulfilled when the, lead has been implanted.

The drug preferably is or contains an anti-inflammatory agent. According to the different preferred embodiments of the method, the lead with the drug-dispensing member 26 is designed to have the features described above.

Although modifications and changes may be suggested by those skilled in the art, it is the invention of the inventors to embody within the patent warranted heron all changes and modifications as reasonably and properly come within the scope of their contribution to the art.

We claim:

1. An electrically conductive lead suitable for implantation in a human or animal body, comprising:
    a proximal end portion adapted for attachment to an electrical medical therapy device;
    a distal end portion having an exterior;
    at least one electrode member disposed at said distal end portion for at least one of emitting and sensing electrical signals associated with said medical therapy;
    an elongated body extending between, and mechanically and electrically connecting, said proximal end portion and said distal end portion;
    a drug-dispensing member disposed at said distal end portion and comprising a drug adapted for release into tissue, said drug-dispensing member having a surface and a configuration so that at least a portion of said surface is exposed at the exterior of said distal end portion and said configuration automatically causing an amount of said drug released into said tissue after implantation to smoothly vary with time from a larger amount to a smaller amount in accordance with a predetermined relationship of the amount of drug released as a function of time; and
    said distal end portion having at least one cavity therein with an opening disposed at said exterior of said distal end portion, and said drug-dispensing member being disposed in said cavity, said cavity having a shape that configures said dispensing member for said automatic control of said release.

2. An electrically conductive lead as claimed in claim 1 wherein said drug comprises an anti-inflammatory agent.

3. An electrically conductive lead as claimed in claim 1 wherein said drug-dispensing member contains respectively different concentrations of said drug in different portions of said drug-dispensing member, causing said automatically controlled release.

4. An electrically conductive lead as claimed in claim 1 wherein said drug-dispensing member is comprised of materials of respectively different compositions of materials that interact with said tissue at respectively different rates, selected from the group consisting of materials that are soluble in body fluids and materials that are resorbable in body fluids, and wherein said different parts are disposed to cause said automatically controlled release.

5. An electrically conductive lead suitable for implantation in a human or animal body, comprising:
    a proximal end portion adapted for attachment to an electrical medical therapy device;
    a distal end portion having an exterior;
    at least one electrode member disposed at said distal end portion for at least one of emitting and sensing electrical signals associated with said medical therapy;
    an elongated body extending between, and mechanically and electrically connecting, said proximal end portion and said distal end portion;
    a drug-dispensing member disposed at said distal end portion and comprising a drug adapted for release into tissue, said drug-dispensing member having a surface and a configuration so that at least a portion of said surface is exposed at the exterior of said distal end portion and said configuration automatically causing an amount of said drug released into said tissue after implantation to smoothly vary with time from a larger amount to a smaller amount in accordance with a predetermined relationship of the amount of drug released as a function of time; and
    said drug dispensing member having a configuration causing a decrease in said amount of said drug released into tissue from a maximum amount released in first hours after implantation to an amount approximately one-third of said maximum amount, occurs over at least 24 hours.

6. An electrically conductive lead as claimed in claim 5 wherein said cavity has a cross-sectional area varying smoothly from a maximum area at said opening to a smaller area at a position in said cavity spaced from said opening.

7. An electrically conductive lead as claimed in claim 6 wherein said cavity has a maximum cross-sectional area at said opening that is at least twice a smallest cross-sectional area of said cavity.

8. An electrically conductive lead as claimed in claim 5 wherein said at least one electrode member has a first surface portion at said exterior of said distal end portion and a second surface portion disposed in an interior of said distal end portion, and wherein said cavity is disposed with said opening in said first surface portion.

9. An electrically conductive lead as claimed in claim 8 wherein said cavity does not extend to said second surface portion and terminates inside of said electrode member.

10. An electrically conductive lead as claimed in claim 8 wherein said cavity extends from said first surface portion and has a minimum cross-sectional area at an intermediate position within said cavity that is smaller than a cross-sectional area of said cavity at a position proximal of said intermediate position.

11. An electrically conductive lead as claimed in claim 5 wherein said distal end portion has a distal end tip and a longitudinal axis, and wherein said cavity is disposed with said opening at said distal end tip and extending in a direction of said longitudinal axis.

12. An electrically conductive lead as claimed in claim 5 wherein said distal end portion has a plurality of cavities therein with respective portions of said drug-dispensing member being disposed in said plurality of cavities, said plurality of cavities, in combination, configuring said drug-dispensing member for said automatically controlled release.

13. An electrically conductive lead as claimed in claim 5 wherein said drug-dispensing member is comprised of a material selected from the group consisting of materials soluble in body fluids and materials resorbable in body fluids.

14. An electrically conductive lead as claimed in claim 5 wherein an entirety of said drug-dispensing member is disposed in said cavity.

15. An electrically conductive lead as claimed in claim 5 wherein said drug comprises an anti-inflammatory agent.

16. An electrically conductive lead as claimed in claim 5 wherein said drug-dispensing member contains respectively different concentrations of said drug in different portions of said drug-dispensing member, causing said automatically controlled release.

17. An electrically conductive lead as claimed in claim 5 wherein said drug-dispensing member is comprised of materials of respectively different compositions of materials that interact with said tissue at respectively different rates, selected from the group consisting of materials that are soluble in body fluids and materials that are resorbable in body fluids, and wherein said different parts are disposed to cause said automatically controlled release.

18. A method for producing an electrically conductive lead adapted for implantation in a human or animal body, comprising the steps of:
mechanically and electrically connecting a proximal end portion, adapted for attachment to an electrical medical therapy device, to a distal end portion having an exterior, with an elongated body portion;
disposing at least one electrode member at said distal end portion adapted for at least one of emitting and sensing electrical signals associated with said medical therapy;
disposing a drug-dispensing member at said distal end portion containing a drug for release into tissue and configuring said dug-dispensing member to expose a portion of a surface of said drug-dispensing member at said exterior of said distal end portion and, by said configuration, automatically controlling release of an amount of said drug into tissue after implantation per time unit to smoothly vary over time from a larger amount to a smaller amount according to a predetermined relationship of the amount of drug released as a function of time; and
providing said distal end portion with at least one cavity therein with an opening disposed at said exterior of said distal end portion, and disposing said drug-dispensing member in said cavity and providing said cavity with a shape that configures said dispensing member for said automatic control of said release.

19. A method as claimed in claim 18 comprising using an anti-inflammatory agent as said drug.

20. A method as claimed in claim 18 comprising providing said drug-dispensing member with respectively different concentrations of said drug in different portions of said drug-dispensing member, causing said automatically controlled release.

21. A method as claimed in claim 18 comprising forming said drug-dispensing member as a plurality of member portions respectively comprising materials of different compositions that interact with said tissue at respectively different rates, and selecting said materials from the group consisting of materials that are soluble in body fluids and materials that are resorbable in body fluids, and disposing said different member portions to cause said automatically controlled release.

22. A method for producing an electrically conductive lead adapted for implantation in a human or animal body, comprising the steps of:
mechanically and electrically connecting a proximal end portion, adapted for attachment to an electrical medical therapy device, to a distal end portion having an exterior, with an elongated body portion;
disposing at least one electrode member at said distal end portion adapted for at least one of emitting and sensing electrical signals associated with said medical therapy;
disposing a drug-dispensing member at said distal end portion containing a drug for release into tissue and configuring said dug-dispensing member to expose a portion of a surface of said drug-dispensing member at said exterior of said distal end portion and, by said configuration, automatically controlling release of an amount of said drug into tissue after implantation per time unit to smoothly vary over time from a larger amount to a smaller amount according to a predetermined relationship of the amount of drug released as a function of time: and
configuring said drug dispensing member to cause a decrease in said amount of said drug released into tissue from a maximum amount released in first hours after implantation to an amount approximately one-third of said maximum amount, occurs over at least 24 hours.

23. A method as claimed in claim 22 comprising providing said cavity with a cross-sectional area varying smoothly from a maximum area at said opening to a smaller area at a position in said cavity spaced from said opening.

24. A method as claimed in claim 23 comprising providing said cavity with a maximum cross-sectional area at said opening that is at least twice a smallest cross-sectional area of said cavity.

25. A method as claimed in claim 22 wherein said at least one electrode member has a first surface portion at said exterior of said distal end portion and a second surface portion disposed in an interior of said distal end portion, and comprising disposing said cavity with said opening in said first surface portion.

26. A method as claimed in claim 25 comprising configuring said cavity so that said cavity does not extend to said second surface portion and terminates inside of said electrode member.

27. A method as claimed in claim 25 comprising extending said cavity from said first surface portion and providing said cavity with a minimum cross-sectional area at an intermediate position within said cavity that is smaller than a cross-sectional area of said cavity at a position proximal of said intermediate position.

28. A method as claimed in claim 22 wherein said distal end portion has a distal end tip and a longitudinal axis, and comprising disposing said cavity with said opening at said distal end tip and extending in a direction of said longitudinal axis.

29. A method as claimed in claim 22 comprising disposing a plurality of cavities in said distal end portion and disposing respective portions of said drug-dispensing member in said plurality of cavities, and configuring said plurality of cavities, in combination, to configure said drug-dispensing member for said automatically controlled release.

30. A method as claimed in claim 22 comprising selecting a material, as said drug-dispensing member, from the group consisting of materials soluble in body fluids and materials resorbable in body fluids.

31. A method as claimed in claim 22 comprising disposing an entirety of said drug-dispensing member in said cavity.

32. A method as claimed in claim 22 comprising using an anti-inflammatory agent as said drug.

33. A method as claimed in claim 22 comprising providing said drug-dispensing member with respectively different concentrations of said drug in different portions of said drug-dispensing member, causing said automatically controlled release.

34. A method as claimed in claim 22 comprising forming said drug-dispensing member as a plurality of member portions respectively comprising materials of different compositions that interact with said tissue at respectively different rates, and selecting said materials from the group consisting of materials that are soluble in body fluids and materials that are resorbable in body fluids, and disposing said different member portions to cause said automatically controlled release.

* * * * *